United States Patent
Xu

(10) Patent No.: US 9,593,101 B2
(45) Date of Patent: Mar. 14, 2017

(54) AVANAFIL PREPARATION METHOD

(71) Applicant: SUZHOU MIRACPHARMA TECHNOLOGY CO., LTD., Suzhou (CN)

(72) Inventor: Xuenong Xu, Suzhou (CN)

(73) Assignee: SUZHOU MIRACPHARMA TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 15/247,383

(22) Filed: Aug. 25, 2016

(65) Prior Publication Data

US 2016/0362400 A1  Dec. 15, 2016

Related U.S. Application Data

(62) Division of application No. 14/948,387, filed as application No. PCT/CN2014/077632 on May 16, 2014, now Pat. No. 9,453,001.

(30) Foreign Application Priority Data

May 23, 2013  (CN) .......................... 2013 1 0195728
May 23, 2013  (CN) .......................... 2013 1 0195854

(51) Int. Cl.
*C07D 403/14*  (2006.01)

(52) U.S. Cl.
CPC .................................. *C07D 403/14* (2013.01)

(58) Field of Classification Search
CPC ..................................................... C07D 403/14
See application file for complete search history.

(56) References Cited

FOREIGN PATENT DOCUMENTS

CN           103254179     *  8/2013  ........... C07D 403/14

* cited by examiner

*Primary Examiner* — Erich A Leeser
(74) *Attorney, Agent, or Firm* — Perkins Coie LLP

(57) ABSTRACT

Disclosed is a method for preparing avanafil (I) by using cytosine as the starting material. The preparation steps comprise: using cytosine as the raw material, and enabling the cytosine to react with side chain 3-chlorine-4-methoxy-benzyl halogen, N-(2-methylpyrimidine)methanamide and S-hydroxymethyl pyrrolidine, to prepare the target product avanafil (I). For the preparation method, the raw material is easily obtained, and the process is simple, economical, and environmentally friendly, so the method meets the requirement of industrial boost.

9 Claims, No Drawings

AVANAFIL PREPARATION METHOD

CROSS REFERENCE TO RELATED APPLICATIONS

This application is a divisional of U.S. patent application Ser. No. 14/948,387 filed Nov. 23, 2015, which is a continuation of PCT/CN2014/077632 filed May 16, 2014, which claims priority to CN 201310195854.5 and CN 201310195728.X, both of which were filed on May 23, 2013. All are incorporated herein by reference.

TECHNICAL FIELD

The present invention relates to the technical field of organic synthesis route design and preparation of API and intermediates, in particular, to the method for preparing avanafil.

BACKGROUND ART

Avanafil is a drug for the treatment of male erectile dysfunction developed by US Vivus Pharmaceutical as authorized by Japan Mitsubishi Tanabe Pharma Corporation. Avanafil is an oral highly-selective phosphodiesterase-5 (PDE-5) inhibitor, which can inhibit the in vivo metabolism of cyclic guanosine monophosphate (CGMP), to strengthen the relaxant effect of smooth muscles and increase the blood flow to the penis, to help erection. Avanafil is approved to appear on the markets by US FDA on Apr. 27, 2012, with the trade name Stendra.

The chemical name of Avanafil (Avanafil, I) is (S)-4-[(3-chloro-4-methoxybenzyl)amino]-2-[2-(hydroxymethyl)-1-pyrrolidinyl]-N-(2-pyrimidylmethyl)-5-pyrimidinecarboxamide.

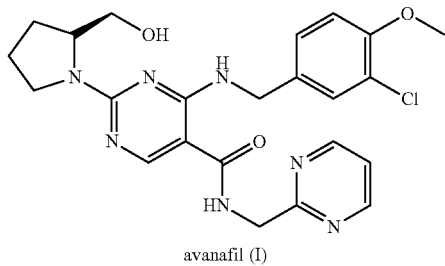

avanafil (I)

The global patent No. WO0183460 and No. WO0119802 for original research of Tanabe Seiyaku reported the preparation method of avanafil and its analogs. According to the method, the avanafil (I) is prepared by the reactions between pyrimidine ring nucleus (X) and the C-2, C-4 and C-5 side chain S-hydroxymethyl pyrrolidine (II), 3-chloro-4-methoxy-benzylamine (VIII) and 2-pyrimidinemethanamine (IX), respectively.

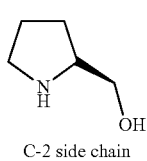

C-2 side chain

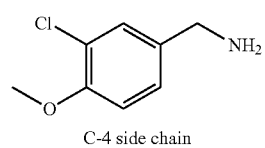

C-4 side chain

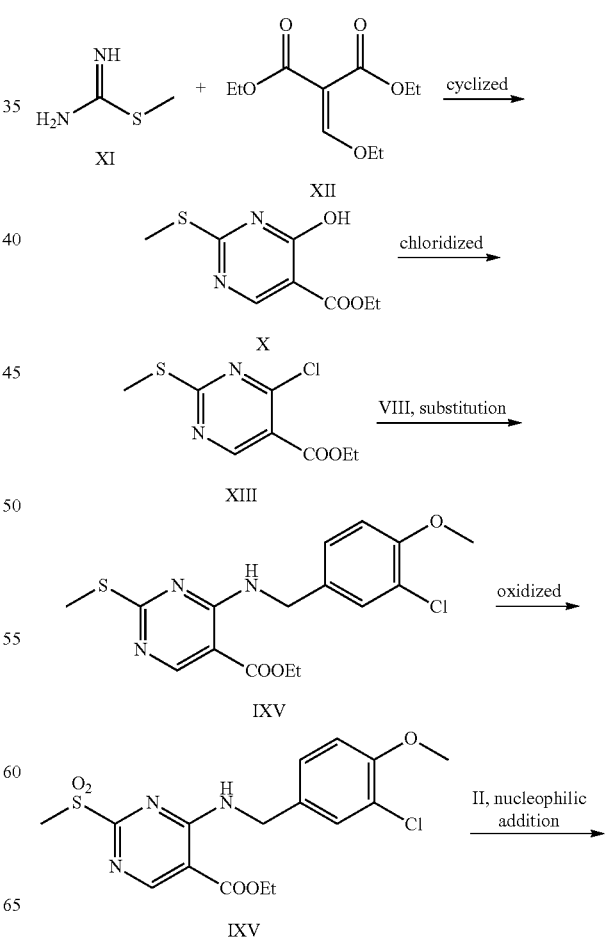

C-5 side chain

Specifically, the cyclization between methyl thiourea (XI) and diethyl ethoxymethylene (XII) occurs to get pyrimidine ring nucleus 4-hydroxy-2-(methylthio)pyrimidine-5-carboxylate (X); the pyrimidine ring nucleus intermediate (X) is chloridized by phosphorus oxychloride to get 4-chloro-2-methylthio-pyrimidine-5-carboxylate (XIII); the intermediate (XIII) and side chains (VIII) have a substitution reaction to get 4-(3-chloro-4-methoxy-benzylamine)-2-methylthio-pyrimidine-5-carboxylate (IXV); then the intermediate (IXV) is oxidized by peroxybenzoic acid to get 4-(3-chloro-4-methoxy-benzylamino)-2-methylthio-pyrimidine oxidized with peracetic acid-5-carboxylate (XV); then the intermediate (XV) and the side chains (II) have a nucleophilic addition reaction to produce 4-[(3-chloro-4-methoxybenzyl)amino]-2-[2-(hydroxymethyl)-1-pyrrolidinyl]pyrimidine-5-carboxylate (XVI); finally the intermediate (XVI) is hydrolyzed and has a acylation reaction with the side chain (IX) to get avanafil (I).

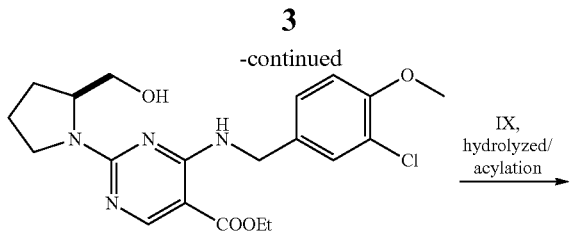

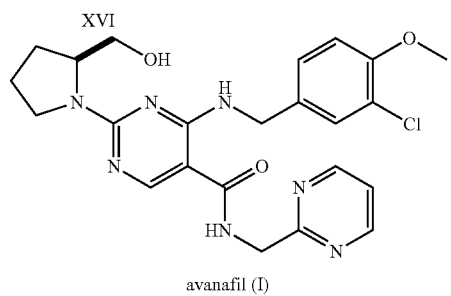

avanafil (I)

The above patent of original research also discloses a method for preparing analogues using 2,4-dichloropyrimidine as a raw material. Under the action of N-butyllithium and diisopropylamine, carbanion forms by 2,4-dichloropyrimidine; under the ultra-low temperature −78° C., it has a nucleophilic addition reaction with carbon dioxide or other carbonyl compounds, to form 5-substituted-2,4-dichloropyrimidine derivative (XVII). The derivative (XVII) reacts with C-2, C-4 and C-5 side chain to prepare the phosphodiesterase-5 (PDE-5) inhibitor with the structure similar to the target compound (I).

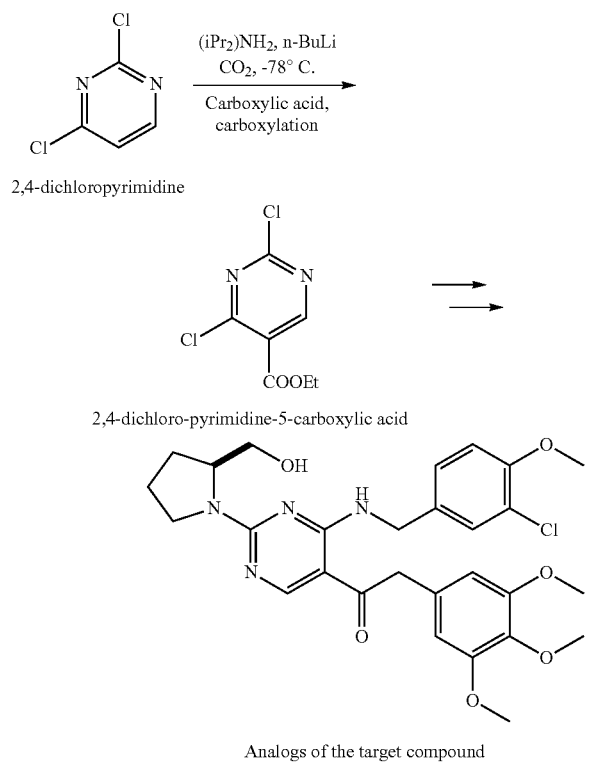

Analogs of the target compound

As shown from above, regardless of using methylthio-substituted pyrimidine or dichloropyrimidine as the staring material, the raw materials used in the preparation process are not readily available, and there are many defects such as many synthesis steps, complex process and difficulty of separation, etc. especially the ultra-low temperature conditions, high-pressure conditions for carbonylation of carbon dioxide and the anhydrous anaerobic conditions for the multi-step reactions of metal reagents, it is difficult to achieve industrialization for the whole synthetic route.

SUMMARY OF THE INVENTION

The object of the present invention is to seek a new preparation approach, to provide an improved method for preparing avanafil according to the concept of atom economy synthesis of green chemistry. This method adopts the very cheap and readily available industrial raw material-cytosine as the starting material, and through halogenation, condensation and substitution, to prepare avanafil. For the preparation method, the process is simple, economical, and environmentally friendly, so the method meets the requirement of industrial production.

To achieve the above object, the present invention provides a main technical solution as follows: A method for preparing avanafil, with the chemical name (S)-4-[(3-chloro-4-methoxybenzyl)amino]-2-[2-(hydroxymethyl)-1-pyrrolidinyl]-N-(2-pyrimidylmethyl)-5-pyrimidinecarboxamide (I),

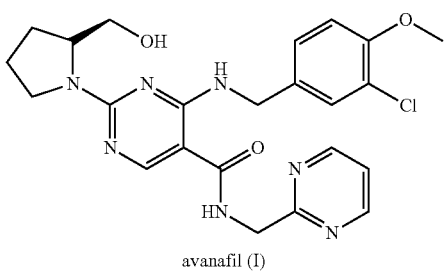

avanafil (I)

Wherein the said preparation method comprises the following steps: using cytosine as raw material, the cytosine and 3-chlorine-4-methoxybenzyl halogen (III) have a substitution reaction to produce N-(3-chloro-4-methoxybenzyl)cytosine (V) which then has a condensation reaction with S-hydroxymethyl pyrrolidine (II) to produce 4-[(3-chloro-4-methoxybenzyl)amino]-2-[2-(hydroxymethyl)-1-pyrrolidinyl]pyrimidine (VI). After halogenation reaction, 4-[(3-chloro-4-methoxybenzyl)amino]-2-[2-(hydroxymethyl)-1-pyrrolidinyl]pyrimidine (VI) and side chain N-(2-methylpyrimidine)methanamide (IV) have an addition reaction to prepare avanafil (I).

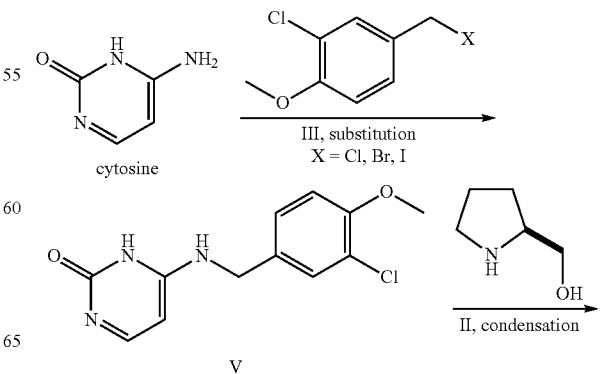

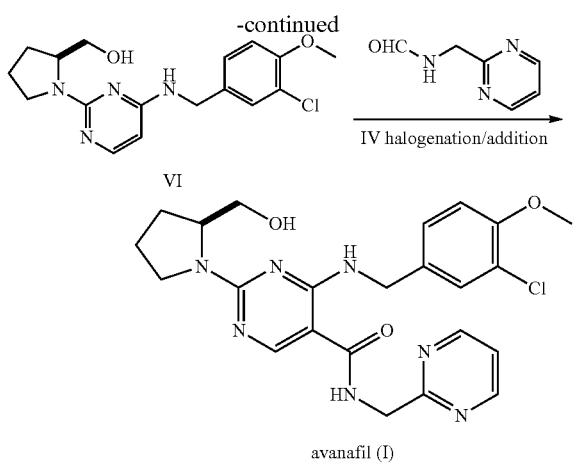

avanafil (I)

In addition, the main technical solution includes the subsidiary technical solutions as follows:

The said halogen X of 3-chlorine-4-methoxybenzyl halogen (III) is chlorine, bromine or iodine.

The said acid-binding agents for substitution reaction are potassium carbonate, potassium hydroxide, potassium tert-butoxide, sodium methoxide, sodium ethoxide, triethylamine, diisopropylamine, pyridine, or sodium hydroxide, preferably triethylamine or pyridine.

The said condensation agents for the condensation reaction are N,N,-dicyclohexyl carbodiimide (DCC), carbonyl diimidazole (CDI), N,N'-diisopropyl carbodiimide (DIC), 1-hydroxy-benzotriazole (HOBt), O-2-(1H-Benzotriazole-1-yl)-1,1,3,3-tetramethyluronium tetrafluoroborate (TBTU), O-(7-Aza-1H-benzotriazole-1-yl)-1,1,3,3-tetramethyluronium hexafluorophosphate (HATU), 7-azabenzotriazole-1-yl)-1,1,3,3-tetramethyluronium hexafluorophosphate (HBTU) or benzotriazol-1-yloxytris (dimethylamino)-phosphonium hexafluorophosphate (BOP), preferably 7-azabenzotriazole-1-yl)-1,1,3,3-tetramethyluronium hexafluorophosphate (HBTU) or benzotriazol-1-yloxytris (dimethylamino)-phosphonium hexafluorophosphate (BOP).

The said alkali accelerators for the condensation reaction are triethylamine, pyridine, 2,6-lutidine, 4-dimethylaminopyridine, N-methylmorpholine, N-ethylmorpholine, diisopropylethylamine, 1,5-diazabicyclo[4.3.0]-non-5-ene, 1,8-diazabicyclo[5.4.0]undec-7-ene or 1,4-diazabicyclo[2.2.2]octane, preferably tris(2,4-di-t-butyl)phenoxy phosphazene.

The temperature of the said condensation reaction is 0-120° C., preferably 50-60° C.

The halogenating agents for the said halogenation reaction are chlorine, liquid bromine, or iodine, preferably liquid bromine, or iodine.

The catalysts for the addition reaction are palladium chloride, palladium acetate, tris(dibenzylideneacetone)dipalladium, nickel chloride, nickel acetate, preferably nickel acetate.

The cocatalysts for the said addition reaction are triphenylphosphine, tri-n-butylphosphine, tri-t-butylphosphine, tricyclohexylphosphine, tri-ethoxy-phosphine, triphenylphosphine oxide, 1,1'-bis(diphenylphosphino)ferrocene, 4,5-bis-diphenyl phosphine-9,9-dimethyl-oxa anthracene or tris(2,4-di-t-butyl)phenoxy phosphazene, preferably tris(2,4-di-t-butyl)phenoxy phosphazene.

To achieve the above object, the present invention also provides another main technical solution as follows: A method for preparing avanafil, comprising the following steps: using cytosine as raw material, the cytosine and 3-chlorine-4-methoxybenzyl halogen (III) have a substitution reaction, to produce N-(3-chloro-4-methoxybenzyl)cytosine (V) which then has an addition reaction with side chain N-(2-methylpyrimidine)methanamide (IV) after halogenation reaction to produce 6-(3-chloro-4-methoxy-benzylamino)-1,2-dihydro-pyrimidin-2-one-5-(N-2-methyl-pyrimidinyl) formamide (VII), and then the said 6-(3-chloro-4-methoxy-benzylamino)-1,2-dihydro-pyrimidin-2-one-5-(N-2-methyl-pyrimidinyl) formamide (VII) and S-hydroxymethyl pyrrolidine (II) have a condensation reaction to produce avanafil (I).

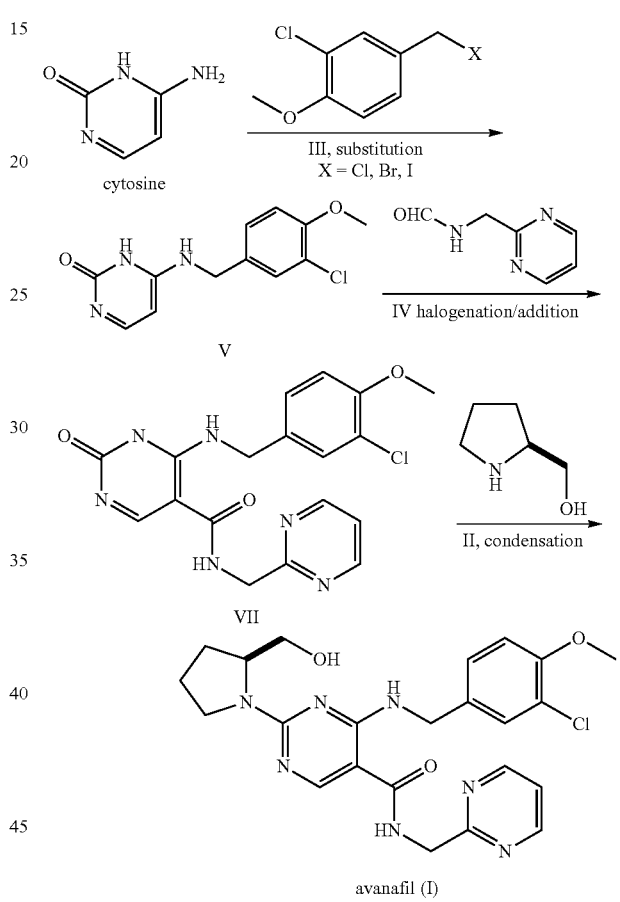

avanafil (I)

In addition, the above main technical solution includes the subsidiary technical solutions as follows:

The said halogen X of 3-chlorine-4-methoxybenzyl halogen (III) is chlorine, bromine or iodine.

The acid-binding agents for the substitution reaction are potassium carbonate, potassium hydroxide, potassium tert-butoxide, sodium methoxide, sodium ethoxide, triethylamine, diisopropylamine, pyridine, or sodium hydroxide, preferably triethylamine or pyridine.

The halogenating agents for the halogenation reaction are chlorine, liquid bromine, or iodine, preferably liquid bromine, or iodine.

The catalysts for the addition reaction are palladium chloride, palladium acetate, tris(dibenzylideneacetone)dipalladium, nickel chloride, nickel acetate, preferably nickel acetate.

The cocatalysts for the said addition reaction are triphenylphosphine, tri-n-butylphosphine, tri-t-butylphosphine, tricyclohexylphosphine, triethoxy phosphine, triphenylphosphine oxide, 1,1'-bis(diphenylphosphino)ferrocene, 9,9-dimethyl-4,5-bis(diphenylphosphino)xanthene or tris(2,4-di-t-butyl)phenoxy phosphazene, preferably tris (2,4-di-t-butyl)phenoxy phosphazene.

The condensation agents for the said condensation reaction are N,N,-dicyclohexyl carbodiimide (DCC), carbonyl diimidazole (CDI), N,N'-diisopropyl carbodiimide (DIC), 1-hydroxy-benzotriazole (HOBt), O-2-(1H-Benzotriazole-1-yl)-1,1,3,3-tetramethyluronium tetrafluoroborate (TBTU), O-(7-Aza- 1H-benzotriazole-1-yl)-1,1,3,3-tetramethyluronium hexafluorophosphate (HATU), 7-azabenzotriazol-1-yl)-1,1,3,3-tetramethyluronium hexafluorophosphate (HBTU) or benzotriazol-1-yloxytris(dimethylamino)-phosphonium hexafluorophosphate (BOP), preferably 7-azabenzotriazol-1-yl)-1,1,3,3-tetramethyluronium hexafluorophosphate (HBTU) or benzotriazol-1-yloxytris(dimethylamino)-phosphonium hexafluorophosphate (BOP).

The alkali accelerators for the said condensation reaction are triethylamine, pyridine, 2,6-lutidine, 4-dimethylaminopyridine, N-methylmorpholine, N-ethylmorpholine, diisopropylethylamine, 1,5-diazabicyclo[4.3.0]-non-5-ene, 1,8-diazabicyclo[5.4.0]undec-7-ene or 1,4-diazabicyclo[2.2.2]octane, preferably Tris(2,4-di-t-butyl)phenoxy phosphazene.

The temperature for the said condensation reaction is 0-120° C., preferably 60-70° C.

Compared to the prior art, the preparation method of avanafil in the present invention uses inexpensive and readily available industrial raw material cytosine as a starting material, and through substitution, condensation and halogenation and addition reactions, the avanafil is prepared. Therefore, the invention has the advantages of easily available raw materials, simple process, economy and environment protection, meeting the requirements for industrial production.

DETAILED DESCRIPTIONS OF THE PREFERRED EMBODIMENTS

The invention is described herein in connection with several embodiments.

Embodiment I 2.22 g of cytosine (20 mmol), 2.0 g of triethylamine (20 mmol), 0.2 g of potassium iodide (1% eq) and 50 mL of anhydrous ethanol were added to a three-necked flask, heated to 50-55° C. and stirred until dissolved to a homogeneous system. 5.60 g of 3-chloro-4-methoxy-benzyl bromide (III) (24 mol) solution was added dropwise to the reaction solution slowly, then heated to 80° C. to continue 3 hours, then the reaction ended with the TLC monitoring. The mixture was cooled down to room temperature, and filtered to remove triethylamine hydrobromide. The filtrate was adjusted to pH 4-5 with hydrochloric acid. Ethanol was recovered under the reduced pressure and residue was recrystallized using ethyl acetate to get 4.78 g off-white solid N-(3-chloro-4-methoxybenzyl)cytosine (V) 4.78 g, with the yield of 90.2%.

Embodiment II

With the protection of nitrogen, 2.65 g of N-(3-chloro-4-methoxybenzyl)cytosine (V) (10 mmol), 6.63 g of benzotriazol-1-yloxytris (dimethylamino)-phosphonium hexafluorophosphate (BOP) (15 mmol) and 50 mL of acetonitrile were added to a three-necked flask. The 1,8-diazabicyclo[5.4.0]undec-7-ene (DBU) (2.28 g, 15 mmol) solution was added dropwise while stirring, and reacted 12 hours at room temperature; then heated to 60° C. for reaction 12 hours. The solvent was removed by distillation under reduced pressure, then added to 100 mL ethyl acetate to dissolve, and washed with 20 mL of 2M sodium hydroxide. The organic phase was separated, dried and concentrated under reduced pressure, then the residue was dissolved in 100 mL of tetrahydrofuran, added with S-hydroxymethyl pyrrolidine (II) (1.31 g, 13 mmol) and sodium hydride (0.32 g, 13 mmol), heated to 55° C. and stirred for reaction for 5 hours, then the reaction ended with the TLC monitoring. After quenching with saturated brine the reaction, the organic phase was separated, dried and distilled under reduced pressure to recover the solvent. The resulting solid was recrystallized with ethanol to get 2.85 g of off-white solid 4-[(3-chloro-4-methoxybenzyl)amino]-2-[2-(hydroxymethyl)-1-pyrrolidinyl]pyrimidine (VI), with the yield of 81.9%.

Embodiment III 1.74 g of 4-[(3-chloro-4-methoxybenzyl)amino]-2-[2-(hydroxymethyl)-1-pyrrolidinyl]pyrimidine (VI) (5 mmol), 0.94 g of liquid bromine (6 mmol) and 25 mL of 2.0M sodium hydroxide solution were added to a microwave reactor for 200 W microwave irradiation for 5 min, cooled down to room temperature, to separate out the white solid; after filtered and dried, added with 25 mL of ethylene glycol dimethyl ether for dissolution and transferred to a three-necked flask. 13 mg of nickel acetate tetrahydrate (0.05 mmol), 32 mg of tris(2,4-di-t-butyl)phenoxy phosphazene (0.05 mmol), 0.54 g of sodium methoxide (10 mmol) and 2.05 g of N-(2-methylpyrimidine)methanamide (IV) (15 mmol) were added, and heated to 120° C. and stirred for reaction for 10 hours under the protection of nitrogen, then the reaction ended with the TLC monitoring. The reaction solution was poured into 25 mL of saturated ammonium chloride solution, extracted three times with ethyl acetate. The organic phase was combined and dried by anhydrous magnesium sulfate. The solvent was recovered under reduced pressure, and the residue was recrystallized with methanol to get 1.96 g of white solid avanafil (I), with the yield of 81.1%.

Embodiment IV 2.56 g of N-(3-chloro-4-methoxybenzyl)cytosine (V) (10 mmol), 3.04 g of iodine (12 mmol) and 50 mL of 2.0M sodium hydroxide solution were added to a microwave reactor for 300 W microwave irradiation for 5 min, cooled down to room temperature, to separate out the white solid; after filtered and dried, added with 50 mL of ethylene glycol dimethyl ether for dissolution and transferred to a three-necked flask. 25 mg of nickel acetate tetrahydrate (0.1 mmol), 64 mg of tris(2,4-di-t-butyl)phenoxy phosphazene (0.1 mmol), 1.08 g of sodium methoxide (20 mmol) and 4.11 g of N-(2-methylpyrimidine)methanamide (IV) (30 mmol) were added, and heated to 110° C. and stirred for reaction for 10 hours under the protection of nitrogen, then the reaction ended with the TLC monitoring. The reaction solution was poured into 50 mL of saturated ammonium chloride solution, extracted three times with ethyl acetate. The organic phase was combined and dried by anhydrous magnesium sulfate. The solvent was recovered under reduced pressure, and the residue was recrystallized with acetone to get 3.35 g of white solid 6-(3-chloro-4-methoxy-benzylamino)-1,2-dihydro-pyrimidin-2-one-5-(N-2-methyl-pyrimidinyl)formamide (VII), with the yield of 83.8%.

Embodiment V

With the protection of nitrogen, 2.0 g of 6-(3-chloro-4-methoxy-benzylamino)-1,2-dihydro-pyrimidin-2-one-5-(N-2-methyl-pyrimidinyl)formamide (VII) (5 mmol), 3.31 g of benzotriazol-1-yloxytris(dimethylamino)-phosphonium hexafluorophosphate (BOP) (7.5 mmol) and 25 mL of acetonitrile in a three-necked flask. 1.15 g of 1,8-diazabicyclo[5.4.0]undec-7-ene (DBU) (7.5 mmol) was added dropwise while stirring, and reacted 12 hours at room temperature; then heated to 60° C. for reaction 12 hours. The solvent was removed by distillation under reduced pressure, then added to 50 mL ethyl acetate to dissolve, and washed with 10 mL of 2M sodium hydroxide. The organic phase was separated, dried and concentrated under reduced pressure, then the residue was dissolved in 50 mL of tetrahydrofuran, added with S-hydroxymethyl pyrrolidine (II) (0.61 g, 6 mmol) and sodium hydride (0.16 g, 6 mmol), heated to 65° C. and stirred for reaction for 5 hours, then the reaction ended with the TLC monitoring. After quenching with saturated brine the reaction, the organic phase was separated, dried and distilled under reduced pressure to recover the solvent. The resulting solid was recrystallized with ethanol to get 1.96 of white solid avanafil (I), with the yield of 81.3%.

The foregoing invention has been described in detail by way of illustration and example for purposes of clarity and understanding As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

What is claimed is:

1. A method for preparing avanafil, with the chemical name (S)-4-[(3-chloro-4-methoxybenzyl)amino]-2-[2-(hydroxymethyl)-1-pyrrolidinyl]-N-(2-pyrimidylmethyl)-5-pyrimidinecarboxamide (I),

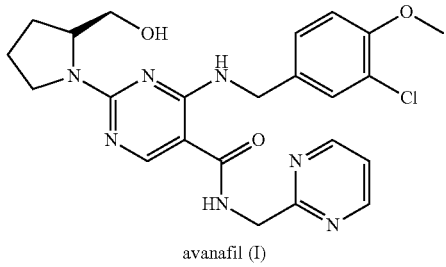

avanafil (I)

Wherein the said preparation method comprises the following steps: using cytosine as raw material, the cytosine and 3-chlorine-4-methoxybenzyl halogen (III) have a substitution reaction to produce N-(3-chloro-4-methoxybenzyl)cytosine (V) which then has a condensation reaction with S-hydroxymethyl pyrrolidine (II) to produce 4-[(3-chloro-4-methoxybenzyl)amino]-2-[2-(hydroxymethyl)-1-pyrrolidinyl]pyrimidine (VI). After halogenation reaction, 4-[(3-chloro-4-methoxybenzyl)amino]-2-[2-(hydroxymethyl)-1-pyrrolidinyl] pyrimidine (VI) and side chain N-(2-methylpyrimidine)methanamide (IV) have an addition reaction to prepare avanafil (I).

2. The method for preparing avanafil according to claim 1, wherein the halogen of 3-chlorine-4-methoxybenzyl halogen (III) is chlorine, bromine or iodine.

3. The method for preparing avanafil according to claim 1, wherein the acid-binding agents for substitution reaction are potassium carbonate, potassium hydroxide, potassium tert-butoxide, sodium methoxide, sodium ethoxide, triethylamine, diisopropylamine, pyridine, or sodium hydroxide.

4. The method for preparing avanafil according to claim 1, wherein the condensation agents for the condensation reaction are N,N,-dicyclohexyl carbodiimide, carbonyl diimidazole, N,N'-diisopropyl carbodiimide, 1-hydroxybenzotriazole, O-2-(1H-Benzotriazole-1-yl)-1,1,3,3-tetramethyluronium tetrafluoroborate, O-(7-Aza-1H-benzotriazole-1-yl)-1,1,3,3-tetramethyluronium hexafluorophosphate, 7-azabenzotriazol-1-yl)-1,1,3,3-tetramethyluronium hexafluorophosphate or benzotriazol-1-yloxytris(dimethylamino)-phosphonium hexafluorophosphate.

5. The method for preparing avanafil according to claim 1, wherein the alkali accelerators for the condensation reaction are triethylamine, pyridine, 2,6-lutidine, 4-dimethylaminopyridine, N-methylmorpholine, N-ethylmorpholine, diisopropylethylamine, 1,5-diazabicyclo[4.3.0]-non-5-ene, 1,8-diazabicyclo[5.4.0]undec-7-ene or 1,4-diazabicyclo[2.2.2]octane.

6. The method for preparing avanafil according to claim 1, wherein the temperature of the condensation reaction is 0-120° C.

7. The method for preparing avanafil according to claim 1, wherein the halogenating agents for the halogenation reaction are chlorine, liquid bromine, or iodine.

8. The method for preparing avanafil according to claim 1, wherein the catalysts for the addition reaction are palladium chloride, palladium acetate, tris(dibenzylideneacetone)dipalladium, nickel chloride, nickel acetate.

9. The method for preparing avanafil according to claim 1, wherein the cocatalysts of the addition reaction are triphenylphosphine, tri-n-butylphosphine, tri-t-butylphosphine, tricyclohexylphosphine, tri-ethoxy-phosphine, triphenylphosphine oxide, 1,1'-bis (diphenylphosphino)ferrocene, 4,5-bis-diphenylphosphine-9,9-dimethyl-oxa anthracene or Tris(2,4-di-t-butyl)phenoxy phosphazene.

* * * * *